United States Patent
Chang et al.

(10) Patent No.: US 6,217,747 B1
(45) Date of Patent: Apr. 17, 2001

(54) PROCESS FOR SELECTIVE WAX HYDROCRACKING

(75) Inventors: Clarence D. Chang, Princeton; Scott Han, Lawrenceville, both of NJ (US); Daniel J. Martenak, Dublin, PA (US); Jose G. Santiesteban, Yardley, PA (US); Dennis E. Walsh, Richboro, PA (US)

(73) Assignee: Mobil Oil Corporation, Fairfax, VA (US)

(*) Notice: Subject to any disclaimer, the term of this patent is extended or adjusted under 35 U.S.C. 154(b) by 0 days.

(21) Appl. No.: 08/150,304

(22) Filed: Nov. 12, 1993

Related U.S. Application Data

(63) Continuation-in-part of application No. 08/095,884, filed on Jul. 22, 1993, now abandoned.

(51) Int. Cl.[7] .......... C10G 47/02; C10G 47/12; C10G 47/04; C10G 47/20
(52) U.S. Cl. .............. 208/112; 208/18; 208/59; 208/89; 208/106; 208/107; 208/108; 208/111; 208/113
(58) Field of Search .............. 208/59, 89, 106, 208/107, 108, 111, 112, 113, 18

(56) References Cited

U.S. PATENT DOCUMENTS

| | | | |
|---|---|---|---|
| 3,682,813 | 8/1972 | Dun et al. | 208/59 |
| 3,755,147 * | 8/1973 | Michelson | 208/112 |
| 3,776,839 | 12/1973 | Ladeur | 208/110 |
| 3,794,580 | 2/1974 | Ladeur | 208/110 |
| 3,803,028 * | 4/1974 | Mead et al. | 208/111 |
| 3,830,273 | 8/1974 | Boileau | 152/352 |
| 3,956,105 * | 5/1976 | Conway | 208/112 |
| 4,283,272 | 8/1981 | Garwood et al. | 208/59 |
| 4,435,275 | 3/1984 | Derr et al. | 208/89 |
| 4,783,576 | 11/1988 | Silver et al. | 174/25 R |
| 4,820,402 | 4/1989 | Partridge et al. | 208/111 |
| 4,918,041 | 4/1990 | Hollstein et al. | 502/217 |
| 4,921,594 * | 5/1990 | Miller | 208/111 |
| 5,113,034 | 5/1992 | Soled et al. | 585/510 |

FOREIGN PATENT DOCUMENTS

| | | |
|---|---|---|
| 1390359 | 4/1975 | (GB) . |
| 1429291 | 3/1976 | (GB) . |
| 1429494 | 3/1976 | (GB) . |
| 1493620 | 11/1977 | (GB) . |
| 1288339 | 11/1989 | (JP) . |

OTHER PUBLICATIONS

*Proceedings 9th International Congress on Catalysis*, vol. 4, 1727–1735 (1988) K. Arata and M. Hino No Month Available.

Hino and Arata, "Synthesis of Solid Superacid of Tungsten Oxide Supported on Zirconia and Its Catalytic Action for Reactions of Butane and Pentane", J. Chem. Soc., Chem. Commun., 1259–1260 (1988) No Month Available.

* cited by examiner

*Primary Examiner*—Elizabeth D. Wood
(74) *Attorney, Agent, or Firm*—Paul E. Purwin

(57) ABSTRACT

A process for hydrocracking heavy hydrocarbon feeds using a catalyst composition containing a hydrogenation/dehydrogenation component, such as a noble metal, and an acidic solid component including a Group IVB metal oxide modified with an oxyanion of a Group VIB metal. The hydrocracking product has high isoparaffin to normal paraffin ratios and with minimal ethane and methane byproducts at high conversions. The hydrocracking step is useful in processes for producing high quality lubricating oil basestocks, along with naphtha and distillate products.

34 Claims, No Drawings

PROCESS FOR SELECTIVE WAX HYDROCRACKING

CROSS-REFERENCE TO RELATED APPLICATIONS

This application is a continuation-in-part of application Ser. No. 08/095,884 filed Jul. 22, 1993 and now abandoned, entitled "Paraffin Isomerization Catalyst and Process for Its Use" incorporated herein in its entirety by reference. This application is further related by subject matter to co-pending application Ser. No. 08/150,303 filed Nov. 12, 1993 entitled "A Process for Naphtha Hydrocracking".

FIELD OF THE INVENTION

This invention relates to a process for the hydrocracking of hydrocarbon feedstocks to produce primarily fuels using a catalyst comprising a hydrogenation/dehydrogenation component, such as a noble metal, and an acidic solid component comprising a Group IVB metal oxide modified with an oxyanion of a Group VIB metal. The invention further relates to a process for co-producing high quality lubricants via hydrocracking wax-containing feeds.

BACKGROUND OF THE INVENTION

Hydrocracking is a process which has achieved widespread use in petroleum refining for converting various petroleum fractions to lighter and more valuable products, especially distillates such as jet fuels, diesel oils and heating oils. Hydrocracking is generally carried out in conjunction with an initial hydrotreating step in which the heteroatom-containing impurities in the feed are hydrogenated without a significant degree of bulk conversion. During this initial step, the heteroatoms, principally nitrogen and sulfur, are converted to inorganic form (ammonia, hydrogen-sulfide) and these gases may be removed prior to the subsequent hydrocracking step although the two stages may be combined in cascade without interstage separation as, for example, in the Unicracking-JHC process and in the moderate pressure hydrocracking process described in U.S. Pat. No. 4,435,275.

In the second stage of the operation, the hydrotreated feedstock is contacted with a bifunctional catalyst which possesses both acidic and hydrogenation/dehydrogenation functionality. In this step, the characteristic hydrocracking reactions occur in the presence of the catalyst. Polycyclic aromatics in the feed are hydrogenated, and ring opening of aromatic and naphthenic rings takes place together with dealkylation. Further hydrogenation may take place upon opening of the aromatic rings. Depending upon the severity of the reaction conditions, the polycyclic aromatics in the feed will be hydrocracked to paraffinic materials or, under less severe conditions, to monocylic aromatics as well as paraffins. Naphthenic and aromatic rings may be present in the product, for example, as substituted naphthenes and substituted polycyclic aromatics in the higher boiling products, depending upon the degree of operational severity.

The bifunctional catalyst used in the hydrocracking process typically comprises a metal component which provides the hydrogenation/dehydrogenation functionality and a porous, inorganic oxide support provides the acidic function. The metal component typically comprises a combination of metals from Groups IVA, VIA and VIIIA of the Periodic Table (IUPAC Table) although single metals may also be encountered. Combinations of metals from Groups VIA and VIIIA are especially preferred, such as nickel-molybdenum, cobalt-molybdenum, nickel-tungsten, cobalt-nickel-molybdenum and nickel-tungsten-titanium. Noble metals of Group VIIIA especially platinum or palladium may be encountered but are not typically used for treating high boiling feeds which tend to contain significant quantities of heteroatoms which function as poisons for these metals.

The porous support which provides the acidic functionality in the catalyst may comprise either an amorphous or a crystalline material or both. Amorphous materials have significant advantages for processing very high boiling feeds which contain significant quantities of bulky polycyclic materials (aromatics as well as polynapthenes) since the amorphous materials usually possesses pores extending over a wide range of sizes and the larger pores, frequently in the size range of 100 to 400 Angstroms (Å) are large enough to provide entry of the bulky components of the feed into the interior structure of the material where the acid-catalyzed reactions may take place. Typical amorphous materials of this kind include alumina and silica-alumina and mixtures of the two, possibly modified with other inorganic oxides such as silica, magnesia or titania.

Zeolitic crystalline materials, especially the large pore size zeolites such as zeolites X and Y, have been found to be useful for a number of hydrocracking applications since they have the advantage, as compared to the non-zeolitic materials, of possessing a greater degree of activity, which enables the hydrocracking to be carried out at lower temperatures at which the accompanying hydrogenation reactions are thermodynamically favored. In addition, the zeolitic crystalline catalysts tend to be more stable in operation than the non-zeolitic materials such as alumina. The zeolitic crystalline materials may, however, not be suitable for all applications since even the largest pore sizes in these materials, typically about 7.4 Å in the X and Y zeolites, are too small to permit access by various bulky species in the feed. For this reason, hydrocracking of residuals fractions and high boiling feeds has generally required a non-zeolitic catalyst of rather lower activity. Although it would be desirable, if possible, to integrate the advantages of the non-zeolitic and the zeolitic crystalline material in hydrocracking catalysts and although the possibility of using active supports for zeolitic crystalline materials has been proposed, the difference in activity and selectivity between the non-zeolitic and zeolitic crystalline materials has not favored the utilization of such catalysts.

The crystalline hydrocracking catalysts based on zeolites such as zeolites X and Y generally tend to produce significant quantities of gasoline boiling range materials (approximately 330° F.–, 165° C.–) materials as product. Since hydrocracked gasolines tend to be of relatively low octane and require further treatment as by reforming before the product can be blended into the refinery gasoline pool, hydrocracking is usually not an attractive route for the production of gasoline. On the other hand, it is favorable to the production of distillate fractions, especially jet fuels, heating oils and diesel fuels since the hydrocracking process reduces the heteroatom impurities characteristically present in these fractions to the low level desirable for these products. The selectivity of crystalline aluminosilicate catalysts for distillate production may be improved by the use of highly siliceous zeolites, for example, the zeolites possessing a silica: alumina ratio of 50:1 or more, as described in U.S. Pat. No. 4,820,402 (Partridge et al), but even with this advance in the technology, it would still be desirable to integrate the characteristics of the amorphous materials with their large pore sizes capable of accommodating the bulky components of typical hydrocracking feeds, with the activity of the zeolite catalysts.

While the considerations set out above apply mostly to fuels hydrocracking processes, they will also be relevant in greater or lesser measure to lube hydrocracking. In the lube hydrocracking process, which is well established in the petroleum refining industry, an initial hydrocracking step is carried out under high pressure in the presence of a bifunctional catalyst which effects partial saturation and ring opening of the aromatic components which are present in the feed. The hydrocracked product is then subjected to dewaxing in order to reach the target pour point since the products from the initial hydrocracking step which are paraffinic in character include components with a relatively high pour point which need to be removed in the dewaxing step.

In theory, as well as in practice, lubricants should be highly paraffinic in nature since paraffins possess the desirable combination of low viscosity and high viscosity index. Normal paraffins and slightly branched paraffins e.g. n-methyl paraffins, are waxy materials which confer an unacceptably high pour point on the lube stock and are therefore removed during the dewaxing operations in the conventional refining process described above. It is, however, possible to process waxy feeds in order to retain many of the benefits of their paraffinic character while overcoming the undesirable pour point characteristic. A severe hydrotreating process for manufacturing lube oils of high viscosity index is disclosed in *Developments in Lubrication PD* 19(2), 221–228, S. Bull et al, and in this process, waxy feeds such as waxy distillates, deasphalted oils and slack waxes are subjected to a two-stage hydroprocessing operation in which an initial hydrotreating unit processes the feeds in blocked operation with the first stage operating under higher temperature conditions to effect selective removal of the undesirable aromatic compounds by hydrocracking and hydrogenation. The second stage operates under relatively milder conditions of reduced temperature at which hydrogenation predominates, to adjust the total aromatic content and influence the distribution of aromatic types in the final product. The viscosity and flash point of the base oil are then controlled by topping in a subsequent redistillation step after which the pour point of the final base oil is controlled by dewaxing in a solvent dewaxing (MEK-toluene) unit. The slack waxes removed from the dewaxer may be reprocessed to produce a base oil of high viscosity index. Processes of this type, employing a waxy feed which is subjected to hydrocracking over an amorphous bifunctional catalyst such as nickel-tungsten on alumina or silica-alumina are disclosed, for example, in British Patents Nos. 1,429,494, 1,429,291 and 1,493,620 and U.S. Pat. Nos. 3,830,273, 3,776,839, 3,794,580, and 3,682,813.

In lube processes of this kind, the catalyst is, like the fuels hydrocracking catalyst, typically a bifunctional catalyst containing a metal hydrogenation component on an amorphous acidic support. The metal component is usually a combination of base metals, with one metal selected from the iron group (Group VIIIA) and one metal from Group VIA of the Periodic Table, for example, nickel in combination with molybdenum or tungsten. The activity of the catalyst may be increased by the use of fluorine, either by incorporation into the catalyst during its preparation in the form of a suitable fluorine compound or by in situ fluoriding during the operation of the process, as disclosed in GB 1,390,359.

Although the lube hydrocracking processes using an amorphous catalyst for the treatment of the waxy feeds has shown itself to be capable of producing high V.I. lubricants, it is not without its limitations. The major process objective in lube hydrocracking (LHDC) is to saturate the aromatic components in the feed to produce saturated cyclic compounds (naphthenes) or, by ring opening of the naphthenes, paraffinic materials of improved lubricating properties. This requires the hydrogenation activity of the catalyst to be high. There is no corresponding requirement for a high level of cracking activity since no major change in boiling range is required or even desirable: the amount of material in the lube boiling range, typically 650° F.+, should be maintained at the maximum level consistent with the degree of ring opening required to furnish a lube product of the desired quality. This combination of requirements has typically led to the use of LHDC catalysts with high metals loadings, particularly for base metal combinations with Group VIA metals such as tungsten: commercial LHDC catalysts currently available have typical nickel loadings of about 5 percent but the tungsten loading may be in the range of 10 to 25 percent.

We have now found that a solid acid catalyst comprising a Group IVB metal oxide modified with an oxyanion of a Group VIB metal may be used as the basis for hydrocracking catalysts. It is an object of the present invention to provide a hydrocracking process using a high activity catalyst. It is a further object of the present invention to provide a hydrocracking process using such a catalyst with products having high isoparaffin/normal paraffin ratios and a low $C_1$–$C_2$ yield.

SUMMARY OF THE INVENTION

There is described herein a catalytic process for hydrocracking hydrocarbon feedstocks generally having an initial boiling point above about 390° F. Catalysts comprising a Group IVB metal oxide modified with an oxyanion of a Group VIB metal have been found to be selective for hydrocracking of waxy feeds with products having high isoparaffin/normal paraffin ratios and with minimal $C_1$–$C_2$ byproducts at high conversions. The catalyst of the present invention shows good potential for high selectivity hydrocracking of waxy feeds with small amounts of light gas.

The invention therefore includes a process for hydrocracking a hydrocarbon feedstock having an initial boiling point above about 390° F. comprising hydrocracking the hydrocarbon feedstock in the presence of hydrogen at a pressure of at least about 500 psig in the presence of a catalyst composition comprising a hydrogenation/dehydrogenation component and an acidic solid component comprising a Group IVB metal oxide modified with an oxyanion of a Group VIB metal, which results in a conversion to 650° F.– products of at least about 10%.

The invention further includes a process for co-producing a lubricating oil base stock which comprises:
(a) hydrocracking a hydrocarbon feedstock in the presence of hydrogen at a pressure of at least about 500 psig in the presence of a catalyst composition comprising a hydrogenation/dehydrogenation component and an acidic solid component comprising a Group IVB metal oxide modified with an oxyanion of a Group VIB metal; and
(b) processing the hydrocracked product to provide a lubricating oil base stock.

Conducting the hydrocracking step in the presence of a catalyst containing a noble metal and an acidic solid component comprising a Group IVB metal oxide modified with an oxyanion of a Group VIB metal results in a hydrocracking product having a high isoparaffin/normal paraffin ratio of generally at least about 2.0 and preferably at least about 3.0. $C_1$ and $C_2$ byproducts are also minimized with generally less than about 0.5% and preferably less than about 0.2% $C_1$ and $C_2$ formed. High conversion, generally about 80 to about 100%, to 650° F.– products can be achieved, if desired, through the process of the present invention.

DETAILED DESCRIPTION OF THE INVENTION

Feedstocks

The hydrocarbon feed materials suitable for use in the hydrocracking step of the present invention include crude petroleum, reduced crudes, vacuum tower residua, vacuum gas oils, deasphalted residua and other heavy oils. These feedstocks contain a substantial amount of components boiling above about 260° C. (about 500° F.) and normally have an initial boiling point of about 290° C. (about 550° F.) and more usually about 340° C. (about 650° F.). Typical boiling ranges will be from about 340° C. to 565° C. (from about 650° F. to about 1050° F.) or from about 340° C. to about 510° C. (from about 650° F. to about 950° F.) but oils with a narrower boiling range can, of course, also be processed, for example, those with a boiling range of from about 340° C. to about 455° C. (from about 650° F. to about 850° F.). Heavy gas oils are often of this kind as are heavy cycle oils and other non-residual materials. Oils obtained from coal, shale or tar sands can also be treated in this way. It is possible to process or co-process materials boiling below about 260° C. (about 500° F.). Feedstocks containing lighter ends of this kind will normally have an initial boiling point above about 200° C. (about 390° F.). Thus, light cycle oils are also suitable for use in the hydrocracking step of the present invention.

When a high quality lube base stock co-product is desired, the selected feedstock will contain a significant amount of waxy components, e.g., at least about 20 weight percent, and preferably at least about 50 weight percent, paraffins. Petroleum waxes, that is, waxes of paraffinic character are derived from the refining of petroleum and other liquids by physical separation from a wax-containing refinery stream, usually by chilling the stream to a temperature at which the wax separates, usually by solvent dewaxing, e.g., MEK/toluene dewaxing or by means of an autorefrigerant process such as propane dewaxing. These waxes have high initial boiling points above about 650° F. (about 345° C.) which render them extremely useful for processing into lubricants which also require an initial boiling point of at least 650° F. (about 345° C.). The presence of lower boiling components is not to be excluded since they will be removed together with products of similar boiling range produced during the processing during the separation steps which follow the characteristic processing steps. Since these components will, however, load up the process units they are preferably excluded by suitable choice of feed cut point. The end point of wax feeds derived from the solvent dewaxing of neutral oils, i.e. distillate fractions produced by the vacuum distillation of long or atmospheric resids will usually be not more than about 1100° F. (about 595° C.) so that they may normally be classified as distillate rather than residual streams but high boiling wax feeds such as petrolatum waxes i.e. the waxes separated from bright stock dewaxing, which may typically have an end point of up to about 1300° F. (about 705° F.), may also be employed.

Feeds also include slack waxes, that is, the waxy product obtained directly from a solvent dewaxing process, e.g. an MEK or propane dewaxing process. The slack wax, which is a solid to semi-solid product, comprising mostly highly waxy paraffins (mostly n- and mono-methyl paraffins) together with occluded oil. The suitable feeds, as defined above, will have $\geq$~95% of their composition boiling point above that of naphtha boiling range materials, e.g., above about 200° C. (about 390° F.) and more generally the boiling point will be above about 300° C. (about 570° F.).

The hydrocarbon feedstock can be treated prior to hydrocracking in order to reduce or substantially eliminate its heteroatom content. As necessary or desired, the feedstock can be hydrotreated under mild or moderate hydroprocessing conditions to reduce its sulfur, nitrogen, oxygen and metal content. Generally, a hydrocarbon feedstock used in hydrocracking should have a low metals content, e.g., less than about 200 ppm, in order to avoid obstruction of the catalyst and plugging of the catalyst bed. The mild to moderate hydrotreating conditions employed include pressures of from about 2 to about 21 MPa and $H_2$ consumptions of from about 20 to about 280 $m^3/m^3$. Conventional hydrotreating process conditions and catalysts can be employed, e.g., those described in U.S. Pat. No. 4,283,272, the contents of which are incorporated by reference herein.

Catalyst

The catalyst used in the process of the present invention comprises an oxide of a Group IVB metal, preferably zirconia or titania. This Group IVB metal oxide is modified in two ways. According to one modification, the Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, 4, 1727–1735 (1988), the entire disclosures of these publications are expressly incorporated herein by reference.

According to another modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst comprises one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, 4, 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the hydrocracking of waxy feeds.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium i-propoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr-O-Zr, further comprising available surface hydroxy groups. These available surface hydroxyl groups are believed to react with the source of an anion of a Group IVB metal, such as tungsten, to form the present acidic catalyst component. As suggested in the aforementioned article by K. Arata and M. Hino in *Proceedings 9th International Congress on Catalysis*, 4, 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, as demonstrated in Examples recited hereinafter, especially in Examples 16–25, refluxing hydrated zirconia in an $NH_4OH$ solution having a pH of greater than 7 was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The hydrogenation/dehydrogenation component of the present catalyst may be derived from Group VIII metals, such as platinum, iridium, osmium, palladium, rhodium, ruthenium, nickel, cobalt, iron and mixtures of two or more thereof. These components may optionally be mixed with components derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The hydrogenation/dehydrogenation component of the catalyst (e.g., Group VIII metal, Group VIIB metal, etc.) may be added after or before the calcination step by techniques known in the art, such as impregnation, coimpregnation, coprecipitation, physical admixture, etc. The hydrogenation/dehydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperatures may not be needed.

In the present catalyst, of the Group IVB oxides, zirconium oxide is preferred; of the Group VIB anions, tungstate is preferred; and of the hydrogenation/dehydrogenation components, platinum and/or platinum-tin are preferred.

Qualitatively speaking, elemental analysis of the present catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt. %, e.g., from about 0.1 to about 2 wt. %, of the hydrogenation/dehydrogenation component, especially when this component is a noble metal.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

It is noted that the present catalyst need not contain any sulfate ion (U.S. Pat. No. 4,918,041), and therefore is expected to be more stable and also to be much easier to regenerate than sulfated catalysts, such as the superacid sulfated catalysts referred to in the aforementioned article by K. Arata and M. Hino in *Proceedings 9th International Congress on Catalysis*, 4, 1727–1735 (1988).

The present catalyst includes a hydrogenation-dehydrogenation component to the catalyst. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIIIA of the Periodic Table (IUPAC Table), either singly, in mixtures or in combination with other metals. The amount of the noble metal component may be in the range 0.001 to 5 wt. % of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the support, it may be done, for example, by treating the support with a platinum metal-containing ion. Suitable platinum compounds include chloroplatinic acid, platinous chloride and various compounds containing the platinum ammine complex. The metal compounds may be either compounds in which the metal is present in the cation or anion of the compound; both types of compounds can be used. Platinum compounds in which the metal is in the form of a cation of cationic complex, e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to convert the metal component to the oxide form and to confer the required mechanical strength on the catalyst. Prior to use the catalyst may be subjected to presulfiding.

When a source of hydrogenation metal, such as $H_2PtCl_6$, is used as a source of a hydrogenation-dehydrogenation component in the present catalyst, it may be desirable to subject the present catalyst to extended reducing conditions, e.g., lasting more than 4 hours.

The present catalyst can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded. The present catalyst may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion of pelletizing into the desired finished catalyst particles.

The catalyst may be treated by conventional pre-sulfiding treatments, e.g., by heating in the presence of hydrogen sulfide, to convert oxide forms of the metal components to their corresponding sulfides. The catalyst may also be treated with gases, such as $H_2$ and $N_2$, at elevated temperatures prior to contacting with feed to improve catalyst activity.

Hydrocracking Conditions

In the hydrocracking step of the present process, the feedstock is contacted with the aforedescribed catalyst in the presence of hydrogen under hydrocracking conditions of elevated temperature and pressure. Conditions of temperature, pressure, space velocity, hydrogen:feedstock ratio and hydrogen partial pressure which are similar to those used in conventional hydrocracking operations can conveniently be employed herein. Process temperatures of from about 175° C. to about 500° C. (from about 350° F. to about 930° F.) can conveniently be used although temperatures above about 425° C. (about 800° F.) will normally not be employed. Generally, temperatures of from about 200° C. to about 425° C. (from about 400° F. to about 800° F.) will be employed. Total pressure is usually in the range of from about 500 to about 20,000 kPa (from about 38 to about 2,886 psig) with pressures above about 7,000 kPa (about 986 psig) normally being preferred. The process is operated in the presence of hydrogen with hydrogen partial pressures normally being from about 600 to about 16,000 kPa (from about 72 to about 2,305 psig). The hydrogen:feedstock ratio (hydrogen circulation rate) will normally be from about 10 to about 3,500 n.l.l-1 (from about 56 to about 19,660 SCF/bbl.). The space velocity of the feedstock will normally be from about 0.1 to about 20 LHSV and preferably from about 0.1 to about 5.0 LHSV. Employing the foregoing hydrocracking conditions, conversion of feedstock to hydrocrackate product can be made to come within the range of from about 10 to about 99 weight percent. The hydrocracking conditions are advantageously selected so as to provide a conversion of from about 15 to about 80, and preferably from about 20 to about 70, weight percent.

The conversion can be conducted by contacting the feedstock with a fixed stationary bed of catalyst, a fixed fluidized bed or with a transport bed. A simple configuration is a trickle-bed operation in which the feed is allowed to trickle through a stationary fixed bed. With such a configuration, it is desirable to initiate the hydrocracking reaction with fresh catalyst at a moderate temperature which is, of course, raised as the catalyst ages in order to maintain catalytic activity.

Processing the Hydrocrackate Product to Provide a Lubricating Oil Base Stock Co-Product When operating at low to moderate conversion, the hydrocrackate product herein can be further processed by one or more downstream operations, themselves known in the art, to provide a high quality lubricating oil base stock co-product. For example, the hydrocrackate can be fractionated by distillation to provide a 650° F.+ fraction which is then subjected to solvent refining (solvent extraction). The details of solvent refining are well known to those skilled in the art and, accordingly, need not be described in detail herein. It is sufficient to note that solvent refining generally consists of contacting, usually in a counter-current fashion, the material to be fractionated with a solvent which has a greater affinity for one of the fractions than the other. Many solvents are available for separating aromatic fractions from paraffinic fractions and the use of all such solvents is considered to be within the scope of the present invention. Although it is believed that solvents such as phenol, furfural, ethylene glycol, liquid sulfur dioxide, dimethyl sulfoxide, dimethylformamide, n-methyl pyrrolidone and n-vinyl pyrrolidone are all acceptable for use as solvents, furfural, phenol and n-methyl pyrrolidone are generally preferred. Further processing of the raffinate stream preferably comprises dewaxing the raffinate employing any of the known dewaxing operations such as, for example, "pressing and sweating", centrifugation, solvent dewaxing and catalytic dewaxing using shape selective zeolites.

Alternatively, a heavy fraction of the hydrocrackate product, e.g., a 650° F.+ fraction, can be directly subjected to solvent dewaxing or catalytic dewaxing in accordance with known procedures to provide a high quality lubricating oil base stock.

The following example illustrates the hydrocracking process of the present invention.

EXAMPLE 1

The tungsten oxide/zirconia catalyst was prepared by impregnating 15 wt. % tungsten as ammonium metatungstate on dry $Zr(OH)_4$. The hydrous zirconia was prepared by dissolving $ZrOCl_2$ in water, precipitating out with $NH_4OH$, and subsequent overnight refluxing of the precipitate in water set to pH~9 with $NH_4OH$. After tungsten impregnation the catalyst was calcined at 825° C. in air for 4 hours. Hexachloroplatinic acid was impregnated on the tungsten/zirconia catalyst (target 0.5 wt. % Pt) and the resultant mixture calcined at 300° C. in air for 2 hours.

The finished catalyst was pelleted and sized at 20/40 mesh. Ten cc. of catalyst was diluted with sand in a 1;1 ratio and charged to a ½" i.d. microreactor. The catalyst was reduced prior to each run by flowing $H_2$ (300 cc/min) at 300° C. for 90 hours. After a standard sulfiding with $H_2S$, the catalyst was contacted with a hydrotreated heavy neutral slack wax feed having the following properties as set forth in Table 1.

TABLE 1

| Hydrotreated Heavy Neutral Slack-Wax Feed Properties | |
|---|---|
| Hydrogen wt. % | 14.97 |
| Sulfur, wt. % | 0.002 |
| Nitrogen, ppm | <5 |
| Pour Point, ° F. | >120 |
| Wax Content, wt. % | 51.4 |
| Paraffins, wt. % | 61.5 |
| Mononaphthenes, wt. % | 21.5 |
| Polynaphthenes, wt. % | 14.1 |
| Aromatics, wt. % | 2.9 |
| Distillation, ° F. | |
| 5% | 454 |
| 10% | 546 |
| 20% | 711 |
| 30% | 786 |
| 50% | 851 |
| 70% | 900 |
| 80% | 929 |
| 90% | 964 |
| 95% | 988 |

Four runs were conducted. The conditions for each run were 1900 psig, 1.0 LHSV and 4000 SCF/BBL $H_2$. The unit temperature was raised to the initial reaction temperature (625° F.) over a 4–6 hour period. After condition changes, at least a 6–8 hour interval preceded material balances. Gas and liquid products were analyzed by gas chromatography. Material balances were 95+%.

Table 2 shows the data from each run. In the first three runs the conversion to 650° F.− was high (at least 80%). The data further shows high iso-/normal ratios for $C_4$–$C_5$ products and ultra-low yield of $C_1$–$C_2$ gas, <0.3 wt. %, at these high conversion conditions. In the fourth run, 21% conversion was achieved at the low operating temperature of 455° F. At this modest conversion level, a solvent dewaxed 650° F.+ lube co-product was obtained in an amount exceeding that of either naphtha or distillate. The lube product properties (viscosity and viscosity index) are characteristic of an extra high quality (XHQ) lube.

TABLE 2

Catalytic Data

| Run | 1 | 2 | 3 | 4 |
|---|---|---|---|---|
| Reactor Temperature, °F. | 625 | 550 | 500 | 455 |
| Net. Conversion to 650° F.-Products, % | 99+ | 99+ | 80 | 21 |
| Yields, wt. % | | | | |
| $CH_4$ | 0.1 | 0.0 | 0.0 | 0.0 |
| $C_2H_6$ | 0.1 | 0.0 | 0.0 | 0.0 |
| $C_3H_8$ | 10.8 | 2.7 | 0.5 | 0.1 |
| iso-$C_4$ | 28.9 | 15.8 | 5.4 | 0.5 |
| n-$C_4$ | 9.9 | 3.4 | 0.9 | 0.1 |
| iso-$C_5$ | 18.3 | 13.3 | 5.1 | 0.5 |
| n-$C_5$ | 6.1 | 2.1 | 0.5 | — |
| $C_6$–330° F. | 25.8 | 62.7 | 41.4 | 5.2 |
| 330–650° F. | — | — | 29.0 | 26.6 |
| 650° F+ | — | — | 17.2 | 67.0 |
| Iso-/Normal Ratio | | | | |
| $C_4$'s | 2.9 | 4.6 | 6.0 | 5.0 |
| $C_5$'s | 3.0 | 6.3 | 10.0 | — |
| 650° F.+ Solvent Dewaxed Lube | — | — | — | — |
| Lube Yield at 0° F. Pour Point, wt. % Feed | — | — | — | 30.5 |
| Kinematic Viscosity (cst@ 100° C.) | — | — | — | 5.2 |
| Viscosity Index at 0° F. Pour Point | — | — | — | 140 |

Changes and modifications in the specifically described embodiments can be carried out without departing from the scope of the invention which is intended to be limited only by the scope of the appended claims.

We claim:

1. A process for hydrocracking a hydrocarbon feedstock having an initial boiling point above about 390° F. comprising hydrocracking the hydrocarbon feedstock in the presence of hydrogen at a pressure of at least about 500 psig in the presence of a catalyst composition comprising:
   a hydrogenation/dehydrogenation catalytic component and an acidic solid catalytic component comprising a Group IVB metal oxide modified with an oxyanion of a Group VIB metal.

2. A process according to claim 1, wherein said hydrogenation/dehydrogenation component comprises a noble metal.

3. A process according to claim 2, wherein said hydrogenation/dehydrogenation component, in addition to said noble metal, further comprises at least one non-noble metal in the form of at least one oxide, hydroxide or metal of at least one element selected from the group consisting of Group VIII metals, Group IVA metals, Group VB metals and Group VIIB metals.

4. A process according to claim 1, wherein said hydrogenation/dehydrogenation component comprises platinum.

5. A process according to claim 2, wherein said hydrogenation/dehydrogenation component further comprises tin.

6. A process according to claim 1, wherein said Group IVB metal oxide comprises zirconia or titania.

7. A process according to claim 1, wherein said Group VIB metal oxyanion is an oxyanion of molybdenum or tungsten.

8. A process according to claim 1, wherein said hydrogenation/dehydrogenation component comprises platinum in the form of an oxide, hydroxide or free metal, said Group IVB metal oxide is zirconium oxide, and said Group VIB metal oxyanion is tungstate.

9. A process according to claim 1, wherein said catalyst comprises a calculated mole ratio of $XO_2/YO_3$, where X is said Group IVB metal and Y is said Group VIB metal, of up to 300 and from 0.001 wt. % to about 5 wt. % of said hydrogenation/dehydrogenation component, based upon the total weight of the catalyst.

10. A process according to claim 8, wherein said catalyst comprises a calculated mole ratio of $XO_2/YO_3$, where X is said Group IVB metal and Y is said Group VIB metal, of from 2 to 100 and from 0.001 wt. % to about 5 wt. % of said hydrogenation/dehydrogenation component, based upon the total weight of the catalyst.

11. A process according to claim 8, wherein said catalyst comprises a calculated mole ratio of $XO_2/YO_3$, where X is said Group IVB metal and Y is said Group VIB metal, of from 4 to 30 and from 0.1 wt. % to about 2 wt. % of platinum, based upon the total weight of the catalyst.

12. The process of claim 1, wherein said hydrocarbon feedstock has an initial boiling point above about of 500° F.

13. The process according to claim 1, wherein said hydrocarbon feedstock is hydrotreated prior to hydrocracking.

14. The process of claim 1, wherein the hydrocracking product comprises less than about 1 wt. % methane and ethane.

15. The process of claim 1, wherein the hydrocracking product has a ratio of isobutane to normal butane of at least about 2:1.

16. The process of claim 1, wherein the hydrocracking product has a ratio of isopentane to normal pentane of at least 2:1.

17. A process for producing a lubricating oil base stock which comprises:
   (a) hydrocracking a hydrocarbon feedstock in the presence of hydrogen at a pressure of at least about 500 psig in the presence of a catalyst composition comprising a hydrogenation/dehydrogenation catalytic component and an acidic solid catalytic component comprising a Group IVB metal oxide modified with an oxyanion of a Group VIB metal; and
   (b) processing the hydrocracked product to provide a lubricating oil base stock.

18. A process according to claim 17, wherein said hydrogenation/dehydrogenation component comprises a noble metal.

19. A process according to claim 18, wherein said hydrogenation/dehydrogenation component, in addition to said noble metal, further comprises at least one non-noble metal in the form of at least one oxide, hydroxide or metal of at least one element selected from the group consisting of Group VIII metals, Group IVA metals, Group VB metals and Group VIIB metals.

20. A process according to claim 17, wherein said hydroqenation/dehydrogenation component comprises platinum.

21. A process according to claim 18, wherein said hydrogenation/dehydrogenation component further comprises tin.

22. A process according to claim 17, wherein said Group IVB metal oxide comprises zirconia or titania.

23. A process according to claim 17, wherein said Group VIB metal oxyanion is an oxyanion of molybdenum or tungsten.

24. A process according to claim 17, wherein said hydrogenation/dehydrogenation component comprises platinum in the form of an oxide, hydroxide or free metal, said Group IVB metal oxide is zirconium oxide, and said Group VIB metal oxyanion is tungstate.

25. A process according to claim 17, wherein said catalyst comprises a calculated mole ratio of $XO_2/YO_3$, where X is said Group IVB metal and Y is said Group VIB metal, of up to 300 and from 0.001 wt. % to about 5 wt. % of said hydrogenation/dehydrogenation component, based upon the total weight of the catalyst.

26. A process according to claim 24, wherein said catalyst comprises a calculated mole ratio of $XO_2/YO_3$, where X is said Group IVB metal and Y is said Group VIB metal, of from 2 to 100 and from 0.001 wt. % to about 5 wt. % of said hydrogenation/dehydrogenation component, based upon the total weight of the catalyst.

27. A process according to claim 24, wherein said catalyst comprises a calculated mole ratio of $XO_2/YO_3$, where X is said Group IVB metal and Y is said Group VIB metal, of from 4 to 30 and from 0.1 wt. % to about 2 wt. % of platinum, based upon the total weight of the catalyst.

28. The process of claim 17, wherein said hydrocarbon feedstock has an initial boiling point above about of 500° F.

29. The process according to claim 17, wherein said hydrocarbon feedstock is hydrotreated prior to hydrocracking.

30. The process of claim 17, wherein at least a portion of the hydrocracking product is subjected to solvent dewaxing.

31. The process of claim 17, wherein at least a portion of the hydrocracking product is subjected to catalytic dewaxing.

32. A process according to claim 1, wherein said Group IVB metal oxide is modified with an acidity increasing amount of said oxyanion of a Group VIB metal.

33. A process according to claim 17, wherein said Group IVB metal oxide is modified with an acidity increasing amount of said oxyanion of a Group VIB metal.

34. A process for hydrocracking a hydrocarbon feedstock having an initial boiling point above about 390° F. comprising hydrocracking the hydrocarbon feedstock in the presence of hydrogen at a pressure of at least about 500 psig in the presence of a catalyst composition comprising a hydrogenation/dehydrogenation component and an acidic solid component comprising a Group IVB metal oxide modified with an oxyanion of a Group VIB metal, wherein said catalyst is prepared by reacting the oxyanion of the Group VIB metal with a hydroxide or oxide of a Group IVB metal and calcining at a temperature in the range of from about 500° C. to about 900° C.

* * * * *